United States Patent [19]

Spencer

[11] Patent Number: 4,651,574

[45] Date of Patent: Mar. 24, 1987

[54] SAMPLE INJECTION MEANS

[76] Inventor: R. Wilson Spencer, P.O. Box 22586, Houston, Tex. 77227

[21] Appl. No.: 720,166

[22] Filed: Apr. 5, 1985

[51] Int. Cl.$^4$ .............................................. G01N 1/10
[52] U.S. Cl. .............................. 73/863.86; 73/864.74; 141/301; 141/330
[58] Field of Search ........... 73/863.86, 863.61, 863.41, 73/864.01, 864, 864.74, 864.73, 863; 141/329, 330, 285, 289, 19, 301, 310; 422/103, 102, 104

[56] References Cited

U.S. PATENT DOCUMENTS

| | | | |
|---|---|---|---|
| 1,842,134 | 1/1932 | Waite | 141/285 |
| 2,797,150 | 6/1957 | Rigby | 73/864.01 |
| 3,438,263 | 4/1969 | Cohen et al. | 73/863.86 |
| 3,484,849 | 12/1969 | Huebner et al. | 141/329 X |
| 3,882,909 | 5/1975 | Ogle | 141/329 X |
| 4,174,632 | 11/1979 | Jansen | 73/864.91 X |
| 4,296,786 | 10/1981 | Brignola | 141/329 X |
| 4,461,185 | 7/1984 | Schoffel | 73/864.01 |
| 4,532,969 | 8/1985 | Kwaan | 141/285 X |

FOREIGN PATENT DOCUMENTS

| | | | |
|---|---|---|---|
| 2204 | of 1926 | Australia | 141/285 |
| 46809 | 4/1889 | Fed. Rep. of Germany | 141/285 |
| 125201 | 11/1901 | Fed. Rep. of Germany | 141/285 |
| 286481 | 8/1915 | Fed. Rep. of Germany | 141/285 |

Primary Examiner—Michael J. Tokar
Assistant Examiner—Tom Noland
Attorney, Agent, or Firm—Robert C. Tucker; William David Kiesel; J. Bradley Overton

[57] ABSTRACT

A sample injection device is provided, comprising a vented needle having a body, the body having an upper end and a lower end, a point on the lower end, an injection passageway running axially through the body and communicating between the upper end and the lower end, and a vent passageway, running through the body and communicating between the lower end and the exterior of the body. The upper end of the body is connectible to a valve, and the lower end is connectible to a receptacle for receiving samples.

9 Claims, 2 Drawing Figures

SAMPLE INJECTION MEANS

BACKGROUND OF INVENTION

1. Field of Invention

This invention relates to sampling devices and, more particularly, to devices which receive samples from a flowing fluid line, such as a process line.

2. Description of Prior Art

In many processes, such as those involved in manufacturing and industrial operations, it is imperative that samples be taken from lines of flowing fluid. It is desirable that such samples be taken so as to avoid contamination of the sample, as well as to avoid contamination of the surrounding environment. Since a minimal disturbance of the process flow is also desirable, the sample is usually taken under pressure by tapping a conduit containing the flowing medium to be samples. This is accomplished by tapping the process line with a sample line and providing a valve which can be opened to allow a sample of the fluid to escape into a sample receptacle. Because of the hazardous nature of many process fluids, it is desirable that human contact with the sample be minimized.

Examples of patented sampling devices may be seen by examining the following patents, which are incorporated herein by reference:

| U.S. Pat. No. | 2,844,964 | (Guibert) |
| U.S. Pat. No. | 2,693,705 | (Casler) |
| U.S. Pat. No. | 3,276,265 | (Taft) |
| U.S. Pat. No. | 3,383,923 | (Conche, et al) |
| U.S. Pat. No. | 3,872,730 | (Ringrose) |
| U.S. Pat. No. | 4,014,216 | (Thorton, et al) |
| U.S. Pat. No. | 4,118,987 | (Zeh) |
| U.S. Pat. No. | 4,174,632 | (Jansen) |
| U.S. Pat. No. | 4,380,176 | (Bauer, et al) |
| U.S.S.R. Patent No. | 549,706 | |

From an examination of the above listed patents, it will become apparent that it is generally known to provide a sampling mechanism whereby sample fluid from a valve passes through a hollow needle, which is inserted through a septum in a removable sample container, thus filling the container. Because a substantial seal is created between the septum and the needle, a vent must be provided in the sample container in order for fluid under pressure to safely enter the container. In Jansen and Zeh, listed above, the vent is proved by a second needle.

The two needle approach described above has proven to be unsatisfactory. By puncturing the septum twice, there is a greater possibility of leakage should the sample container be over-filled. Substances, such as hazardous acids, etc., would then contaminate and possibly damage process equipment, pollute the environment and possibly injure the personnel involved in collecting the sample. Also, the needles disclosed in the prior art are beveled so as to produce a sharp edge which cuts as it penetrates a septum. This cutting action results in a poor seal between the needle and the septum, further resulting in an increased probability of leakage.

Also, the presence of two needles has created the problem of multiple punctures in the septum as a sample container is repeatedly removed and then re-installed. Looking at the Zeh patent, for example, if the sample container were rotated slightly and then re-installed, the needles would pierce the septum at different points, resulting in leakage through the original puncture holes in the septum. The Jansen device attempted to solve this problem by providing side-by-side needles which are centered so as to pierce the septum in the same place, regardless of the rotational position of the sample container. This arrangement has also proven unsatisfactory, in that an inadequate seal is formed when the two needles are reinserted into the same puncture hole.

SUMMARY OF THE INVENTION

Accordingly, it is an object of this invention to provide a sample injection means which minimizes sample leakage while allowing adequate venting of the sample container.

It is another object of this invention to provide a sample injection means which penetrates a septum with a single needle, and which minimizes the cutting of the septum.

Therefore, a sample injection means is provided, comprising a vented needle having a body, the body having an upper end and a lower end, a point on the lower end, an injection passageway running axially through the body and communicating between the upper end and the lower end, and a vent passageway, running through the body and communicating between the lower end and the exterior of the body. The upper end of the body is connectible to a valve and the lower end is connectible to a receptacle for receiving samples.

The above and other objectives and advantages of the invention will become apparent from the following description when considered with the accompanying drawings.

DETAILED DESCRIPTION OF PREFERRED EMBODIMENTS OF THE INVENTION

Figures 1, 2:
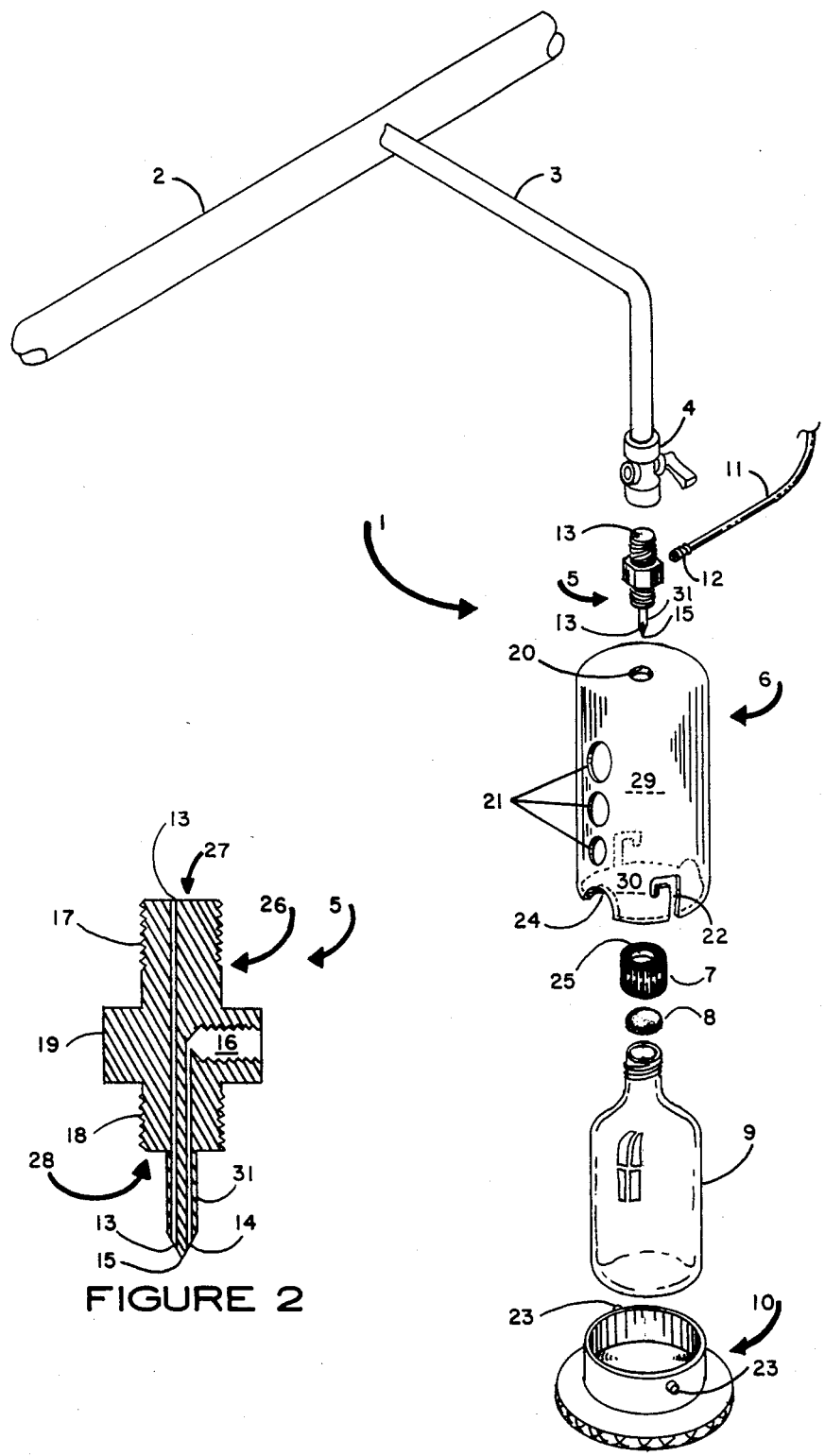
FIG. 1 is an exploded perspective view of a preferred embodiment of the invention.
FIG. 2 is a sectional view of a preferred embodiment of the invention.

As shown in FIG. 1, the sample injection means 1 is connectible to a process line 2 by means of a sample line 3 and valve 4. A vented needle 5 is connectible to the valve 4, preferably by a threaded valve fitting 17.

As shown in greater detail in FIG. 2, the vented needle 5 comprises a solid body 26 having an upper end 27 and a lower end 28. A needle shaft 31, preferably cylindrical, is machined onto lower end 28. At the end of needle shaft 31 is a point 15, which is preferably conical in shape, and preferably forming an acute angle of 20° with the longitudinal axis of the needle 5. Threaded shroud fitting 18 is machined onto lower end 28 for attachment to a shielding means, such as shroud 6. Injection passageway 13 transmits sample fluid through the needle 5. Vent passageway 14 vents gases and excess sample fluids from sample bottle 9 to vent line opening 16, to which may be attached a vent line fitting 12, which, in turn, is attachable to a vent line 11. Vent line 11 may lead to a closed waste container or may be coupled with valving and a pressure reducing mechanism, such as a venturi, in order to return the contents of the vent line 11 to the process line 2. Wrench fitting 19 may be machined onto needle 5 as shown, to facilitate installation.

As can be seen, point 15 will penetrate a septum 8 in opening 25 of sample bottle cap 7. The conical shape of point 15, coupled with the location of the emergence of passageways 13 and 14 above the point 15, minimizes the cutting of the septum 8 which occurs with prior art devices. It is preferable, for effective sealing, that septum 8 be composed of chemically resistant elastomers of the chemical group hexafluoropropylene vinylidene fluoride. Septums of natural rubber, buna-n (nitride), silicone, buna-s or neoprene are much less effective. Also, it has been found that a septum thickness of ⅛ inch is preferable.

As a safety measure, a shroud 6 may be provided. A top opening 20 in shroud 6 receives shroud fitting 18. Shroud 6 should envelope sample bottle 9 in order to provide a maximum shield from sample spillage or bottle breakage. Bottom opening 30 in shroud 6 allows for insertion of sample bottle 9. Shroud cavity 29 may be shaped so as to accommodate various sizes of sample bottles 9. However, it is preferred that cavity 29 closely correspond to the external dimensions of bottle 9 so as to assure the centering of bottle 9, and thus the centering of point 15 so as to penetrate septum 8 in the same place regardless of the degree of rotation of bottle 9. Inspection ports 21 are provided to aid in preventing over-filling of bottle 9 while maximizing the shielding effect of shroud 6. Bottle handling slots 24 are provided to aid in installation and removal of sample bottles 9.

Shroud cap 10 provides a closure for bottom opening 30, assuring maximum safety. Shroud cap 10 is removably attachable to shroud 6, by means of locking pins 23 and j-slots 22.

Thus, as can be seen, a sample injection means 1 is provided which accomplishes sampling and venting with a single vented needle 5, resulting in safer, more efficient sampling. Environmental contamination is minimized. By providing venting outside of shroud 6, contamination of the exterior of sample bottle 9 is also reduced. Vented needle 5 is easily adaptable to fit many sampling devices. Applications for the device include the sampling of hazardous materials and known carcinogens such as benzene, carbon tetrachloride, sulfuric acid and the like; fuming materials, such as monochloroacetic acid; and biological compounds, such as gene-spliced microorganisms. While the above embodiments of the invention have been defined in specific terms, it will be obvious to those skilled in the art that variation may be made without departing from the spirit and scope of the invention, as defined by the following claims.

I claim:

1. A sample injection means, comprising a single vented needle having a unitary body, said body having an upper end and a lower end, an axially symmetrical conical point on said lower end, an injection passageway, running axially through said body and communicating between the exterior of said upper end and the exterior of said conical point above the vertex of said point, and a vent passageway, running through said body and communicating between an endpoint located on the exterior of said conical point above the vertex of said point and the exterior of said body above said endpoint and below the exterior of said upper end when in use said upper end being connected to a valve and said lower end being connected to a receptacle for receiving samples.

2. A sample injection means according to claim 1, further comprising a shroud having an interior cavity communicating with a bottom opening, said cavity and bottom opening being of sufficient size to receive a sample bottle, said shroud also having a top opening communicating between the exterior of said shroud and said cavity and connectable to said lower end of said body such that said vent passageway emerges from said body exterior to said shroud.

3. A sample injection means according to claim 2, further comprising a shroud cap, removably attachable to said shroud so as to close said bottom opening of said shroud.

4. A sample injection means according to claim 3, wherein said shroud is provided with at least one inspection port, communicating between said cavity and the exterior of said shroud.

5. A sample injection means according to claim 4, further comprising a vent line connectible to said needle body so as to communicate with said vent passageway.

6. A sample injection means according to claim 2, further comprising a sample bottle, a bottle cap, removably attachable to said bottle and having an opening therein, and a septum composed of a chemically resistant elastomer from the chemical group hexafluoropropylene vinylidene fluoride, insertable between said bottle cap and said bottle.

7. A sample injection means according to claim 6, further comprising a shroud cap, removably attachable to said shroud so as to close said bottom opening of said shroud.

8. A sample injection means according to claim 7, wherein said shroud is provided with at least one inspection port, communicating between said cavity and the exterior of said shroud.

9. A sample injection means according to claim 8, further comprising a vent line, connectible to said needle body so as to communicate with said vent passageway.

* * * * *